(12) United States Patent
Wang et al.

(10) Patent No.: US 8,791,039 B2
(45) Date of Patent: Jul. 29, 2014

(54) AGGLOMERATED ZEOLITE ADSORBENTS AND PROCESS FOR PRODUCING THE SAME

(75) Inventors: Huiguo Wang, Beijing (CN); Jianfeng Ma, Beijing (CN); Dehua Wang, Beijing (CN); Zhuo Yu, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 814 days.

(21) Appl. No.: 12/865,267

(22) PCT Filed: Jan. 24, 2009

(86) PCT No.: PCT/CN2009/000117
§ 371 (c)(1),
(2), (4) Date: Nov. 22, 2010

(87) PCT Pub. No.: WO2009/097747
PCT Pub. Date: Aug. 13, 2009

(65) Prior Publication Data
US 2011/0105301 A1    May 5, 2011

(30) Foreign Application Priority Data
Jan. 31, 2008    (CN) .......................... 2008 1 0057262

(51) Int. Cl.
*B01J 29/06*    (2006.01)
*B01J 20/00*    (2006.01)

(52) U.S. Cl.
USPC .................. 502/60; 502/62; 502/63; 502/64; 502/68; 502/79; 502/400; 502/407; 502/410; 502/411

(58) Field of Classification Search
USPC ............. 502/60, 62, 63, 64, 68, 79, 400, 407, 502/410, 411
See application file for complete search history.

(56) References Cited

U.S. PATENT DOCUMENTS

| | | | |
|---|---|---|---|
| 3,119,660 A * | 1/1964 | Howell et al. ................. | 423/710 |
| 3,878,129 A | 4/1975 | Rosback | |
| 3,960,774 A | 6/1976 | Rosback | |
| 3,997,620 A | 12/1976 | Neuzil | |
| 4,283,587 A | 8/1981 | Rosback et al. | |
| 4,603,040 A * | 7/1986 | Kuznicki et al. .............. | 423/712 |
| 4,940,548 A | 7/1990 | Zinnen | |
| 5,149,887 A | 9/1992 | Zinnen | |
| 5,174,979 A * | 12/1992 | Chao et al. ........................ | 95/96 |
| 6,143,057 A * | 11/2000 | Bulow et al. ..................... | 95/96 |
| 6,306,363 B1 | 10/2001 | Funakoshi et al. | |
| 6,410,815 B1 | 6/2002 | Plee et al. | |
| 6,425,940 B1 * | 7/2002 | Chao et al. ..................... | 95/130 |
| 6,530,974 B2 * | 3/2003 | Plee ................................ | 95/99 |
| 6,652,626 B1 * | 11/2003 | Plee ................................ | 95/96 |
| 6,884,918 B1 | 4/2005 | Plee et al. | |
| 2002/0038603 A1 * | 4/2002 | Plee ................................ | 95/96 |

FOREIGN PATENT DOCUMENTS

| | | |
|---|---|---|
| CN | 1275926 A | 12/2000 |
| CN | 1339334 A | 3/2002 |
| CN | 1347339 A | 5/2002 |
| CN | 1358566 A | 7/2002 |
| CN | 1448213 A | 10/2003 |
| CN | 1448338 A | 10/2003 |
| CN | 1552515 A | 12/2004 |
| CN | 1565718 A | 1/2005 |
| EP | 0960854 A1 | 12/1999 |
| JP | 2007238484 A | 9/2007 |

OTHER PUBLICATIONS

English translation of CN 1358566, Jul. 2002.*
English language abstract of CN 1339334 A.
International Search Report for PCT/CN2009/000117 dated Mar. 24, 2009.
English language Abstract of CN 1275926A, dated Jan. 21, 2011.
English language Abstract of CN 1347339A, dated Mar. 7, 2011.
English language Abstract of CN 1358566A, dated Jan. 21, 2011.
English language Abstract of CN 1448213A, dated Jan. 21, 2011.
English language Abstract of CN 1448338A, dated Jan. 21, 2011.
English language Abstract of CN 1552515A, dated Mar. 7, 2011.
English language Abstract pf CN 1565718A, dated Jan. 21, 2011.
English language Abstract of EP 0960854A, dated Jan. 21, 2011.
English language Abstract of JP 2007238484A, dated Mar. 7, 2011.

* cited by examiner

*Primary Examiner* — Elizabeth Wood
(74) *Attorney, Agent, or Firm* — Finnegan, Henderson, Farabow, Garrett & Dunner, LLP

(57) ABSTRACT

An agglomerated zeolite adsorbent which comprises 95-99.5 mass % of X zeolite and 0.5-5.0 mass % of binder, wherein the exchangeable cationic sites of said X zeolite are occupied by Group IIA metal and/or K, the total pore volume of said adsorbent is no less than 0.26 mL/g as measured by mercury porosimetry, the volume of pores with pore diameters from 100 to 500 nm is at least 60% based on the total pore volume. During shaping, a pore-forming agent is added to this adsorbent, and then the adsorbent is alkali treated for in-situ crystallization, followed by ion exchange. Said adsorbent has high adsorption capacity, fast mass transfer rate and good mechanical strength. Said adsorbent is suitable for liquid phase adsorptive separation of para-xylene from $C_8$ aromatic hydrocarbons and is also suitable for adsorptive separation of other alkyl aromatic hydrocarbons isomers.

19 Claims, 1 Drawing Sheet

AGGLOMERATED ZEOLITE ADSORBENTS AND PROCESS FOR PRODUCING THE SAME

FIELD OF THE INVENTION

The present invention relates to an agglomerated zeolite adsorbent and process for producing the same, more specially, to an adsorbent for adsorptive separation of isomers of aromatic hydrocarbons and a process for producing the same.

BACKGROUND OF THE INVENTION

In producing aromatic hydrocarbons compounds having multi-substituents, mixed products in which various isomers are simultaneously present are generally obtained due to the limit of reaction process and reaction thermodynamical equilibrium. Said mixed products are necessary to be further separated to obtain the most valuable isomers for application. However, these isomers usually have very close boiling points such that it is difficult to separate them using conventional rectification process. In this case, selective adsorption is widely used in industry to achieve the separation of these isomers.

The principle of adsorptive separation technique is that an object product is separated from mixed materials and purified by certain adsorbents with characteristics of preferentially adsorbing or preferentially non-adsorbing the object product, in combination with suitable processes. Adsorbent is the basis and core of adsorptive separation technique. Now, it is known that X zeolite, ion exchanged with barium cation or potassium cation, alone or in combination, has a characteristic of preferentially adsorbing para-aromatic hydrocarbons isomers. BaX or BaKX thus is used widely as adsorbents in industry to adsorb p-xylene so as to separate it from $C_8$ aromatic hydrocarbons isomers, in combination with continuous countercurrent simulation moving bed. P-xylene is obtained in high purity as following: p-xylene is adsorbed by an adsorbent in adsorbing column through repeating countercurrent mass transfer exchange utilizing the adsorbent's characteristic of preferentially adsorbing p-xylene, so that its concentration increases gradually; the adsorbed p-xylene is desorbed with a desorbent after desired product purity is achieved; and extracting solution is rectified to recover the desorbent. P-xylene produced by the process has a purity of up to 99.8 mass % and the yield is up to 98 mass %. In addition, U.S. Pat. No. 4,940,548 and U.S. Pat. No. 5,149,887 disclose that such adsorbents are used for separating isomers of diethyltoluene, methylphenol and the like.

An excellent adsorbent should have three properties, including high adsorption capacity, good selective adsorption ability and faster mass transfer speed. It is obvious that adsorption capacity of the adsorbent is proportional to the content of zeolite herein, that is, the higher is the content of zeolite, the greater is the adsorption capacity of the adsorbent. Since synthesized zeolite is usually in form of powder, it is necessary to agglomerate it by adding certain amount of binder in order to meet the requirement in industry, thereby resulting in partial loss of adsorption capacity. Therefore, reducing the amount of inert binder used in the adsorbent and converting it into zeolite as much as possible is an effective way to improve adsorption performance. U.S. Pat. No. 3,960,774 firstly discloses that an adsorbent precursor containing X or Y zeolite and binder is treated with an aqueous sodium hydroxide solution in order to improve the crystallinity of the adsorbent, and then is ionexchanged with barium or potassium cations.

The selectivity of the adsorbent is improved mostly in respect of the species of exchanged ions and the property of the zeolite. In U.S. Pat. No. 3,997,620, SrBaX adsorbent is prepared from exchanging with strontium and barium bi-metal ions to improve the selectivity for para-xylene. In U.S. Pat. No. 4,283,587, ionexchanged X or Y zeolite is treated with alkyl amine or alkyl ammonium hydrochloride to improve the selectivity for para-isomers. CN1275926A discloses an agglomerated zeolite adsorbent, wherein X zeolite having a Si/Al atomic ratio of 1-1.15 and low content of silicon dioxide is used as raw material to prepare adsorbent, and is exchanged with barium and potassium ions. Exchangeable sites of the adsorbent are at least 70% occupied by barium ions, and up to 30% occupied by potassium ions. Kaolin is used as the binder of said adsorbent, and this adsorbent is treated with an alkaline liquor in order to be crystallizated into X zeolite in-situ, thereby enhancing the capability of the adsorbent.

To improve the performance of the adsorbent, the mass transfer rate of the adsorbent should be improved besides improving adsorption capability and selectivity of the adsorbent. In CN1448213A and CN1565718A, X zeolites of small crystal grains with the crystal particulate size of 0.5-1.0 micron or 0.1-0.4 micron are used as active components of adsorbents in order to improve the mass transfer rate in crystallines of zeolites of the adsorbents.

CN1358566A discloses an adsorbent and its preparation process wherein the performance of the adsorbent is improved by improving the secondary pore distribution of the adsorbent. X zeolite or Y zeolite is mixed with binder, and 0.5-6.0 mass % of pore-expanding agent is added into the resulted mixture, following by mixing homogeneously, moulding by adding water, drying, activating, alkali treating and ion exchanging, to obtain an adsorbent. Said binder is one or more selected from kaolin, bentonite, bentone, silica sol, aluminium sol and water glass. Said pore-expanding agent is one or more selected from lignin, sodium cellulose and sesbania powder.

DESCRIPTION OF THE INVENTION

The object of the present invention is to provide an agglomerated zeolite adsorbent and a process for producing the same. Said adsorbent has higher adsorption capacity and faster mass transfer rate.

The agglomerated zeolite adsorbent according to the present invention comprises 95-99.5 mass % of a X zeolite and 0.5-5.0 mass % of a binder. The exchangeable cationic sites of said X zeolite are occupied by Group IIA metal and/or K. The total pore volume of said adsorbent is no less than 0.26 mL/g as measured by mercury porosimetry, wherein the volume of pores with pore diameters from 100 to 500 nm is at least 60%.

In accordance with the present invention, a pore-forming agent is added to the mixed powder during the preparation of an adsorbent to produce the agglomerated adsorbent rich in inter-crystalline packing pore channels after crystal transformation. The proportion of macropore is high, as measured by mercury porosimetry. The pore volume is large, and the mass transfer performance is good. Both the utilization efficiency of zeolite in the adsorbent and the extent of in-situ crystallization reaction of clay during alkali treating are enhanced, and thereby the adsorption capacity of the adsorbent is significantly increased, in turn the production capacity per unit mass of the adsorbent is increased together with maintaining good mechanical strength.

MODE OF CARRYING OUT THE INVENTION

Figure 1:
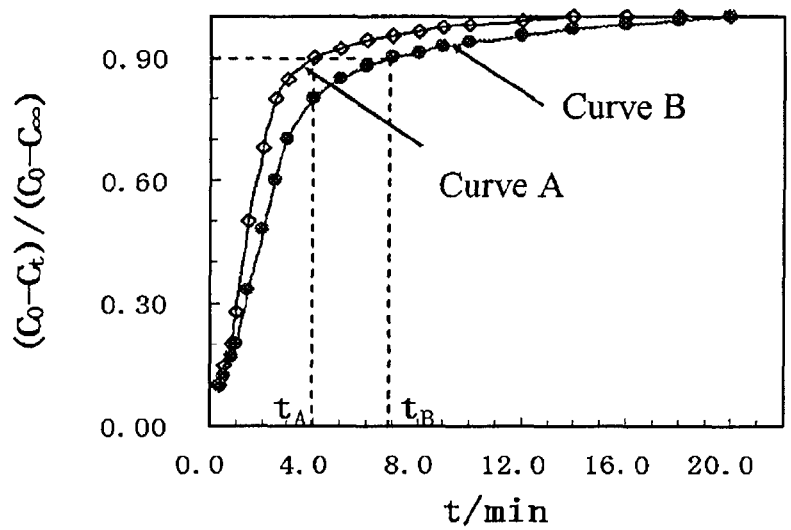
FIG. 1 is a schematic figure of diffusion profile for evaluating the mass transfer rate of the adsorbent according to the present invention.

In accordance with the present invention, X zeolite and a zeolitizable clay are mixed, shaping auxiliary agents are added, and a pore-forming agent is added, preferably an aqueous solution of a pore-forming agent is sprayed, during pellet-shaping, thereafter the pore-forming agent is removed by calcining and being decomposed into volatile components. As a result, a rich pore channel system is formed inside the agglomerated pellets, and the pore volume of final adsorbent is not less than 0.26 mL/g, as measured by mercury porosimetry, wherein the volume of pores with pore diameters from 100 nm to 500 nm is at least 60%, and the volume of pores with pore diameters larger than 500 nm is from 5% to 15%, preferably from 9% to 15%, based on the total pore volume. Said adsorbent has a good mass transfer performance, thus the time required for reaching adsorption equilibrium is reduced significantly and the utilization efficiency of the zeolite inside the adsorbent particle is increased. In addition, the original crystalline structure of the clay is destroyed and converted to amorphous aluminum silicate having reactivity due to calcination of agglomerated pellets at high temperature. Most of the amorphous aluminum silicate is further converted into X zeolite by alkali treatment under suitable conditions, thereby obtaining agglomerated adsorbent particles comprising at least 95 mass % of X zeolite. Meanwhile, transformation by alkali treatment further causes the formation of more compact bindings among crystalline grains inside the pellets, so as to render the adsorbent having good mechanical strength.

In accordance with the present invention, the proportion of large pores with certain pore diameters and the total pore volume of the adsorbent are measured using mercury porosimetry. As measured by mercury porosimetry, the total pore volume of the adsorbent according to the present invention is preferably no less than 0.28 mL/g, the volume of pores with pore diameters from 100 nm to 500 nm is preferably at least 70% based on the total pore volume.

Exchangeable cationic sites of X zeolite in said adsorbent are occupied by Group IIA metals and/or K, wherein the Group IIA metal is preferably barium. When cations of X zeolite in said adsorbent are Ba and K, the molar ratio of barium oxide to potassium oxide in the adsorbent is from 20 to 60, preferably from 30 to 50. The amount of sodium oxide in the adsorbent should be no more than 1.0 mass %, preferably no more than 0.6 mass %. The amount of water in the adsorbent is expressed by ignition loss after calcination at 600° C. for 2 hours. In general the ignition loss of the adsorbent is controlled no more than 7.0 mass %, preferably from 4.0 mass % to 6.0 mass %.

To enhance the mass transfer rate of the adsorbent, said adsorbent of the present invention is selected from X zeolite having small crystal grains which have the mean particulate size from 0.1 micron to 2.0 microns, preferably from 0.2 micron to 1.0 micron.

The binder in said adsorbent is the un-crystallized matrix of kaoline group minerals left after in-situ crystallization, where said kaoline group minerals are kaolinite, dickite, nacrite, endellite or mixture thereof.

The present invention provides a process for producing an adsorbent, including the following steps:

(1) combing zeolite NaX or NaKX with zeolitizable clay and shaping auxiliary to provide a mixed powder, wherein the mass ratio of zeolite NaX or NaKX to zeolitizable clay is 88-95:12-5, adding water-soluble carbonate or water-soluble polymer compound as a pore-forming agent to the mixed powder to allow it to be agglomerated into pellet by tumbling, followed by drying and calcining;

(2) treating the calcined pellet of step (1) with sodium hydroxide solution or mixed solution of sodium hydroxide and sodium silicate at 90-100° C. to allow the clay therein to be crystallized into zeolite X in situ, followed by drying and calcining;

(3) cation-exchanging the resultant of step (2) with solution of soluble salt of Group IIA metal or with mixed solution of potassium salt and soluble salt of Group IIA metal, followed by activation.

In said process, step (1) is the shaping of the adsorbent. Zeolite NaX or NaKX is mixed with a zeolitizable clay in a predetermined ratio with shaping auxiliary being added to form a mixed powder, and the mixed powder as prepared is tumbled for shaping. The used equipment for shaping by tumbling includes turnplate, sugar-coat pot or rolling barrel. During the shaping, the mixed powder is placed in the tumbling equipment, then water is sprayed onto the mixed powder during tumbling to allow it to be agglomerated gradually into pellets and growing bigger. When pellets are shaped into a certain particle size, they are taken out of the shaping equipment. Then pellets with diameter of 0.2-1.5 mm, preferably 0.35-0.80 mm, are obtained by sieving, and then are dried and calcined to give shaped pellets.

It is preferred that the zeolitizable clay in step (1) is kaolin family mineral. Preferably said kaolin family minerals are kaolinite, dickite, nacrite, endellite or mixture thereof.

Preferably said shaping auxiliary is selected from one or more compound of lignin, sesbania powder, dry starch powder, carboxymethyl cellulose, and activated carbon. The ratio between the mass of the shaping auxiliary added and the total mass of the zeolite NaX or NaKX and the binder is from 1% to 8%, preferably from 2% to 5%.

The pore-forming agent in step (1) is selected from water-soluble carbonates or water-soluble polymer compounds, which is removed from the adsorbent as volatile component during calcining. Preferably said water-soluble carbonates are ammonium carbonate, sodium carbonate or sodium bicarbonate. Preferably said water-soluble polymer compounds are one or more compound selected from the group consisting of polyacrylamide, polyvinyl alcohol and polyethylene glycol. Preferably, the aqueous solution of pore-forming agent is used in step (1). The concentration of aqueous pore-forming agent solution is from 0.5 mass % to 10.0 mass %, preferably from 1.0 mass % to 8.0%. Instead of water, an aqueous solution formulated from the pore-forming agent is preferably sprayed onto the mixed powder during shaping. Aqueous solution of pore-forming agent added is from 10% to 40%, preferably from 20% to 30%, based on the total mass of the mixed powder.

In said process, step (2) is to treat the shaped and calcined pellets from step (1) with alkali to allow the zeolitizable clay therein to be crystallized into zeolite X in situ. During the in-situ crystallization treatment, the ratio by volume of liquid/solid is from 1.2 to 2.0:1. The alkaline liquor used in the in-situ crystallization treatment is selected from sodium hydroxide solution or mixed solution of sodium hydroxide and sodium silicate. When the alkaline liquor used is sodium hydroxide solution, the concentration thereof is preferably from 1.0 mol/L to 4.0 mol/L. When the alkaline liquor used is mixed solution of sodium hydroxide and sodium silicate, the content of sodium oxide in this mixed solution is from 3.0 mass % to 8.0 mass %, and the content of silicon dioxide is from 1.0 mass % to 7.0 mass %. The treatment time for in-situ crystallization is preferably from 3 hours to 10 hours. After in-situ crystallization, the resulting pellets are dried and calcined.

The drying temperature in steps (1) and (2) is preferably from 60° C. to 120° C., and the drying time is preferably from 4 hours to 12 hours. The calcination temperature is preferably from 500° C. to 700° C., and calcination time is preferably from 2 hours to 6 hours.

In said process, step (3) is to cation-exchange the in-situ crystallizated pellets so as to convert the cationic sites of zeolite X therein into Group IIA metal and/or K. As a result, electrostatic field properties inside the crystal interstices of zeolites are regulated, and the adsorption selectivity is increased. Said cation exchanging can be carried out in tank vessel or column vessel, preferably a exchanging column in continuous mode. The exchanging temperature is preferably from 60° C. to 160° C., more preferably from 90° C. to 100° C. The volume space velocity of exchanging liquor is from 1.0 $h^{-1}$ to 12.01 $h^{-1}$, preferably from 2.0 $h^{-1}$ to 6.0 $h^{-1}$. The exchanging time is from 5 hours to 40 hours, preferably from 10 hours to 20 hours. The molar ratio between the cations in the exchange liquor and the sodium ions in the zeolite, i.e., the exchange ratio, is from 1.5 to 5.0. When an adsorbent comprising both Group IIA metal and potassium is desired, a mixed solution of potassium salt and soluble salt of Group IIA metal can be used for the cation exchange. Alternatively, a solution of soluble salt of Group IIA metal is first used for exchanging, and then a solution of potassium salt is used for potassium exchanging. Cation-exchanged pellets require washing before activation to remove free metal ions. Said activation is preferably carried out under flowing air or nitrogen gas to remove water from the adsorbent. The activation temperature is preferably from 180° C. to 250° C., and the activation time is preferably from 2 hours to 12 hours.

Said soluble salt of Group IIA metal used for ion exchange is preferably soluble salt of barium, such as barium nitrate or barium chloride. Said potassium salt used for ion exchange is preferably potassium chloride or potassium nitrate.

The silica/alumina ratio of zeolite X in said adsorbent, i.e., the molar ratio of silicon oxide to aluminum oxide in zeolite should be low so as to enhance the adsorption selectivity of the adsorbent. The silica/alumina ratio of zeolite X used is preferably from 2.0 to 2.4.

Zeolite X used for preparing the adsorbent of the present invention is preferably zeolite X in small crystal grains, wherein mean size of crystal grains is 0.1-1.0 micron. There are many methods for preparing zeolite X in small crystal grains, such as those described in CN 1448338A and EP 960854A1.

The adsorbents prepared according to the present invention are suitable for liquid phase adsorptive processes for the separation of aromatic hydrocarbons isomers. More specifically, the adsorbents are suitable for the separation of aromatic hydrocarbons isomers with di-substituents at para-positions from the mixture of isomers, for example, the adsorptive separation of para-xylene from a mixture of ortho-xylene, meta-xylene, para-xylene and ethylbenzene. It can also be used in adsorptive separation of isomers of diethylbenzene, isomers of diethyltoluene, or isomers of methylphenol. Said liquid phase adsorptive separation may be operated in multiple columns in series, or operated in a simulated moving bed accomplished by a rotary valve or an electromagnetic valve stack. The operating pressure of adsorptive separation is preferably from 0.5 MPa to 1.6 MPa, and the temperature is preferably from 120° C. to 200° C.

While embodiments of the present disclosure are described in connection with the above embodiments and the corresponding text and figures, there is no intent to limit the disclosure to the embodiments in these descriptions. On the contrary, the intent is to cover all alternatives, modifications, and equivalents included within the spirit and scope of embodiments of the present disclosure.

The present invention will be further illustrated with reference to the following examples, but not limited thereby.

The methods for measuring the content of zeolite X in the adsorbents in examples and the data for evaluating performance are as follows:

The content of zeolite X in the adsorbents is calculated by measuring the adsorptive capacity of toluene in sample under certain conditions. The measurement conditions are as follows: in a thermostatic waterbath of 35° C., a flow of nitrogen gas entrained with toluene vapour under normal pressure passes through the adsorbents until absorption saturation is achieved, wherein the relative pressure of toluene vapour (the ratio of partial pressure of toluene to the saturation vapor pressure of toluene at the tested temperature) is 0.5; and the content of zeolite X is predetermined as 100 mass % when the adsorptive capacity of toluene is 0.235 gam per gram of sample.

The mechanical strength of the adsorbents is characterized by crash percentage under pressure, and the measuring method is as follows: a certain amount of adsorbent saturated naturally in air is weighed and placed into stainless steel cartridge whose bottom is closed. A cylinder pin matched with the stainless steel cartridge is placed on the adsorbent, and then placed on a particle strength measurer and pressed up to 250 N. The adsorbent is taken out after pressure is released, and is sieved through a sieve with meshes of 0.3 mm. The pellets which can not pass through the sieve are weighed. The percentage of the mass reduction of sample after sieving based on the mass of sample before compression is defined as the crash percentage under pressure of sample to be measured. The lower the crash percent is, the better the strength of sample is.

The pore volume and the size distribution of pores of the adsorbent sample are measured using Autopore II-9220 mercury porosimeter from Micromeritics Company in USA, according to ASTM D4382-03.

The method for measuring the mass transfer rate for internal diffusion of the adsorbent is as follows: 3-4 g adsorbent sample, which has been dried and cooled under nitrogen gas after activation by dehydration, is fed into an equilibrium tank with magnetic stirring, and at the same time 15 mL ortho-xylene is added. The tank is closed, and stands for 4 hours at 120° C. so that the adsorbent is saturated sufficiently with ortho-xylene. Then the magnetic stirring is turned on, and 15 mL para-xylene is injected quickly. At the same time timing is started, and a small amount of liquid sample in the equilibrium tank is taken out immediately. Its composition is analysed by gas chromatography for calculating the initial concentration $C_0$ of para-xylene in the mixed solution. A small amount of liquid sample is taken out at intervals and its composition is analysed for calculating corresponding concentration $C_t$ of para-xylene. Keep taking samples until the composition of the liquid in the equilibrium tank doesn't change, i.e., diffusive equilibrium being reached, and at this time the concentration of para-xylene in solution is recorded as $C_\infty$. With sampling time t as horizontal coordinate and $(C_0-C_t)/(C_0-C_\infty)$ as longitudinal coordinate, the diffusion profile is obtained as showed in FIG. 1. As can be seen from FIG. 1, internal diffusion of para-xylene is divided into fast stage and slow stage, and the initial rate of diffusion is fast, while the rate of diffusion slows down significantly as it is close to equilibrium. As a result, there is a inflexion point approximately at $(C_0-C_t)/(C_0-C_\infty)=0.9$ in the curve. In order to compare the difference of mass transfer rates among different adsorbent samples, diffusion time corresponding to $(C_0-C_t)/(C_0-C_\infty)=0.9$ is used as index for judging mass transfer rate of adsorbent, which is referred to as mass transfer rate for internal diffusion. The shorter the period in which $(C_0-C_t)/(C_0-C_\infty)$ reaches to 0.9 is, the better the mass transfer performance of the sample is. For example, the mass transfer rate for internal diffusion of adsorbents A and B may be calculated as $t_A$ and $t_B$ from the diffusion profile of adsorbents A and B showed in FIG. 1. For $t_A$ is smaller than $t_B$, it indicates that the mass transfer performance of adsorbent A is better than that of adsorbent B.

Example 1

The adsorbent of the present invention was prepared and its adsorptive performance was measured.
(1) Production of Zeolites X in Small Crystal Grains:

16.4 kg sodium meta-aluminate solution (the content of $Al_2O_3$ is 17.3 mass %, and the content of $Na_2O$ is 21.0 mass %), 11.0 kg deionized water and 2.9 kg sodium hydroxide were added into a 100 L synthesis tank. After solid base was completely dissolved under stirring, 11.8 kg sodium silicate solution (the content of $SiO_2$ is 28.3 mass %, and the content of $Na_2O$ is 8.8 mass %) was added. The mixture was stirred until it was uniform, and stands for aging at 25° C. for 20 hours to give a guiding agent.

255 kg sodium silicate solution, 1001 kg deionized water and 37 kg sodium hydroxide were added into a 2000 L tank at 25° C., and they were sufficiently mixed under stirring. 227 kg sodium meta-aluminate was added under stirring, then 15 kg guiding agent was added. Keep stirring until uniform mixture was achieved. The mixture was warmed to 100° C., and stands for crystallization for 4 hours. The product was washed with water until the pH value of washing solution was less than 10. The product was filtered and then dried for 12 hours at 80° C. to give NaX zeolite. The molar ratio of $SiO_2/Al_2O_3$ of the zeolite was 2.19 as calculated from unit cell constants, and the mean particulate size of crystal grains was 0.7 micron as observed by scanning electron microscope.
(2) Shaping by Tumbling:

88 kg (on dry basis, the same hereinafter) NaX zeolite produced in step (1) was mixed homogeneously with 9 kg kaolin (produced from Linfen, Shanxi, China, the content of kaolinite is 90 mass %) and 3.4 kg sesbania powder to give mixed powder. The mixed powder was placed in a turnplate. During tumbling, a suitable amount of aqueous sodium carbonate solution with a concentration of 5.0 mass % was sprayed onto the powder, so that the solid mixed powder was agglomerated into pellets. The amount of aqueous sodium carbonate solution sprayed during tumbling was 25 mass % of the solid mixed powder. Pellets with diameters of 0.35-0.80 mm were obtained by sieving, which were dried at 80° C. for 10 hours and calcined at 540° C. for 4 hours under air stream.
(3) In-Situ Crystallization:

The above-mentioned calcined pellets were treated with 1.5 mol/L sodium hydroxide solution in a volume ratio of liquid/solid of 2.0:1, and stand for 4.0 hours at 96° C. to allow kaolin therein to crystallize into zeolite X in situ. The pellets obtained after in-situ crystallization were washed with deionized water until the pH value of washing solution was 9.0. After drying at 80° C. for 12 hours and calcining at 500° C. for 2 hours, its adsorptive capacity of toluene was 0.225 g/g, which was equivalent to 95.7 mass % of the content of zeolite X in agglomerated pellets.
(4) Ion Exchange:

After in-situ crystallization and calcination, the pellets were ion-exchanged continuously in a conventional column with 0.18 mol/L barium nitrate solution as exchange liquor. The barium ion-exchange was carried out under normal pressure at 92° C. for 10 hours, and the volume space velocity of exchange liquor was 4.0 $h^{-1}$. The volume ratio of barium nitrate solution used to the pellets was 40:1. After exchange, the pellets were washed with deionized water whose volume was 10 times of the volume of pellets, and were dried under nitrogen gas stream at 220° C. for 6 hours to give adsorbent A-1. Its ignition loss was 4.3 mass %, as measured after calcination at 600° C. for 2 hours. The composition of the adsorbent, the volume and the size distribution of pores as measured by mercury porosimetry, and other physical properties were recorded in table 1.

Example 2

The adsorbent was produced according to the procedure described in example 1, except that: in the step (2) for shaping by tumbling, 5.0 mass % aqueous ammonium carbonate solution was sprayed in an amount of 28 mass % based on the solid mixed power; in the step (3), the calcined pellets were treated with mixed solution of sodium hydroxide and sodium silicate for in-situ crystallization, wherein said mixed solution comprises 4.3 mass % of $Na_2O$ and 2.1 mass % of $SiO_2$ and the toluene adsorption capacity of agglomerated pellets obtained after in-situ crystallization was 0.230 g/g, which was equivalent to 97.9 mass % of the content of zeolite X in agglomerated pellets. Adsorbent A-2 was obtained after ion-exchange and activation and was calcined at 600° C. for 2 hours, and the ignition loss was 4.5 mass %. The composition of the adsorbent, the volume and the size distribution of pores as measured by mercury porosimetry, and other physical properties were recorded in table 1.

Example 3

The adsorbent was produced according to the procedure described in example 1, except that: in the step (2), 63 kg NaX zeolite as produced in example 1 was mixed homogeneously with 5.4 kg kaolin and 2.7 kg carboxymethyl cellulose (available from Qingquan Cellulose plant in Qingzhou, Shandong, China). The mixture was placed in turnplate, and sprayed with a suitable amount of aqueous solution of polyacrylamide (available from Henghao Innovation Amide Ltd., Shanghai, China) with a concentration of 2.0 mass % during tumbling to allow the solid mixed powder to be agglomerated into pellets. The amount of aqueous polyacrylamide solution sprayed during tumbling was 20 mass % of the solid mixed powder. Drying, calcination and in-situ crystallization were carried out according to the subsequent steps described in example 1. The toluene adsorption capacity of pellets obtained after in-situ crystallization was measured as 0.226 g/g, which was equivalent to 96.2 mass % of the content of zeolite X in agglomerated pellets.

After in-situ crystallization, the pellets were ion-exchanged with barium nitrate solution according to the procedure described in the step (4) of example 1, except that the pellets washed with water after ion-exchange were dried for 6 hours under nitrogen gas stream at a temperature of 200° C. to obtain adsorbent A-3 and the ignition loss was 5.6 mass % as measured after calcination at 600° C. for 2 hours. The composition of the adsorbent, the volume and the size distribution of pores as measured by mercury porosimetry, and other physical properties were recorded in table 1.

Example 4

The adsorbent was produced according to the procedure described in example 1, except that: in the step (2), 63 kg NaX zeolite as produced in example 1 was mixed homogeneously with 5.4 kg kaolin and 2.7 kg carboxymethyl cellulose. The mixture was placed in turnplate, and sprayed with a suitable amount of aqueous solution of polyvinyl alcohol (available from Shaorong Trade Ltd., Shanghai, China) with a concentration of 2.0 mass % during tumbling to allow the solid mixed powder to agglomerate into pellets. The amount of aqueous solution of polyvinyl alcohol sprayed during tumbling was 22 mass % of the solid mixed powder. Drying, calcination and in-situ crystallization were carried out according to the subsequent steps described in example 1. The toluene adsorption capacity of pellets obtained after in-situ crystallization was measured as 0.224 g/g, which was equivalent to 95.3 mass % of the content of zeolite X in agglomerated pellets.

After in-situ crystallization, the pellets were ion-exchanged with barium nitrate solution according to the step (4) of example 1, except that the pellets washed with water after ion-exchange were dried for 6 hours under nitrogen gas stream at a temperature of 200° C. to obtain adsorbent A-4 and the ignition loss was 5.3 mass % as measured after calcination at 600° C. for 2 hours. The composition of the adsorbent, the volume and the size distribution of pores as measured by mercury porosimetry, and other physical properties were recorded in table 1.

Example 5

NaKX zeolite was produced according to the method described in EP 0960854A1. 5.5 kg sodium meta-aluminate solution (the content of $Al_2O_3$ was 17.3 mass %, and the content of $Na_2O$ is 21.0 mass %), 12.6 kg deionized water and 7.4 kg sodium hydroxide were added into a 100 L synthesis tank. After the solid base was completely dissolved under stirring, 19.6 kg sodium silicate solution (the content of $SiO_2$ is 28.3 mass %, and the content of $Na_2O$ is 8.8 mass %) was added. The mixture was stirred until it was uniform, then it stands for aging at 40° C. for 1.0 hour to obtain a guiding agent. 198 kg sodium silicate solution, 660 kg deionized water, 90 kg sodium hydroxide and 105 kg potassium hydroxide were added into a 2000 L tank at 40° C., and they were sufficiently mixed under stirring. 288 kg sodium metaaluminate was added under stirring, and then 3 kg guiding agent was added. A uniform mixture was obtained by stirring. At 40° C. the mixture was stirred for aging for 4 hours at 250 U/min. Then the mixture was warmed up to 70° C., and stands for crytallisation for 4 hours. Keep washing the product with water until the pH value of washing solution was less than 10. The product was filtered, and dried at 70° C. for 12 hours to obtain NaKX zeolite. The molar ratio of $SiO_2/Al_2O_3$ in the zeolite was 2.03 as calculated from unit cell constants, and the mean particulate size of crystal grains was 0.4 micron as observed by scanning electron microscope.

75 kg NaKX zeolite, 8.3 kg kaolin and 3.0 kg carboxymethyl cellulose were mixed homogeneously to obtain mixed powder. The mixed powder was placed in turnplate, and sprayed with aqueous ammonium carbonate solution with a concentration of 5.0 mass % during tumbling to allow the solid mixed powder being agglomerated into pellets. The amount of aqueous ammonium carbonate solution sprayed during tumbling was 27 mass % of the solid mixed powder. Drying, calcination and in-situ crystallization were carried out according to the subsequent steps described in example 1. The toluene adsorption capacity of pellets obtained after in-situ crystallization was measured as 0.228 g/g, which was equivalent to 97.0 mass % of the content of zeolite X in agglomerated pellets.

After in-situ crystallization, the pellets were ion-exchanged with barium nitrate solution according to the step (4) of example 1, except that the pellets washed with water after ion-exchange were dried for 4 hours under nitrogen gas stream at a temperature of 230° C. to obtain adsorbent A-5 and the ignition loss was 4.2 mass % as measured after calcination at 600° C. for 2 hours. The composition of the adsorbent, the volume and the size distribution of pores as measured by mercury porosimetry and other physical properties were recorded in table 1.

Example 6

The adsorbent was produced according to the procedure described in example 5, except that the pellets obtained after in-situ crystallization were ion-exchanged with mixed solution of potassium chloride and barium nitrate as exchange liquor wherein $K^+$ ion concentration was 0.1 mol/L and $Ba^{2+}$ ion concentration was 0.20 mol/L. In ion-exchange, the ratio by volume of exchange liquor consumed to solid pellets was 40:1. Adsorbent A-6 as produced comprises 0.75 mass % of potassium oxide and 45 mass % of barium oxide. The molar ratio of barium oxide to potassium oxide in adsorbent A-6 as produced was 36.8. Ignition loss for adsorbent A-6 was 4.8 mass %, as measured after calcination at 600° C. for 2 hours. The composition of the adsorbent, the volume and the size distribution of pores as measured by mercury porosimetry, and other physical properties were recorded in table 1.

Comparative Example 1

70 kg NaX zeolite as produced in example 1 was mixed homogeneously with 7 kg kaolin. The mixture was placed in turnplate, and sprayed with a suitable amount of deionized water during tumbling to allow the solid powder being agglomerated into pellets. The amount of water sprayed during tumbling was 30 mass % of the solid powder. Pellets with a size of 0.35-0.80 mm were obtained by sieving. These pellets were dried at 80° C. for 10 hours, and calcined at 540° C. for 4 hours under air stream. The calcined pellets were treated with mixed solution of sodium hydroxide and sodium silicate for in-situ crystallization, wherein said mixed solution comprises 4.3 mass % $Na_2O$ and 2.1 mass % $SiO_2$. After in-situ crystallization, the pellets obtained were washed with deionized water until the pH value of washing solution was 9.0. Then the pellets were dried at 80° C. for 12 hours, and calcinated at 500° C. for 2 hours. Toluene Adsorption capacity of the agglomerated pellets was 0.219 g/g, which was equivalent to 93.2 mass % of the content of zeolite X in agglomerated pellets.

The pellets obtained after in-situ crystallization treatment were ion-exchanged and dried for dehydration according to the step (4) of example 1 to obtain comparative adsorbent B-1, and its ignition loss was 4.7 mass % as measured after calcination at 600° C. for 2 hours. The composition of the adsorbent, the volume and the size distribution of pores as measured by mercury porosimetry, and other physical properties were recorded in table 1.

Comparative Example 2

70 kg NaX zeolite as produced in example 1 was mixed homogeneously with 7 kg kaolin and 2.8 kg carboxymethyl cellulose to produce mixed powder. The mixed powder was placed in turnplate, and sprayed with a suitable amount of deionized water during tumbling to allow the solid powder being agglomerated into pellets. The amount of water sprayed during tumbling was 32 mass % of the solid mixed powder. Pellets with a size of 0.35-0.80 mm were obtained by sieving. These pellets were dried for 10 hours at 80° C., and then calcined for 4 hours at 540° C. under air stream. The calcined pellets were treated with mixed solution of sodium hydroxide and sodium silicate for in-situ crystallization, wherein said mixed solution comprises 4.3 mass % $Na_2O$ and 2.1 mass % $SiO_2$. After in-situ crystallization, the pellets obtained were washed with deionized water until the pH value of washing solution was 9.0. The pellets were dried for 12 hours at 80° C., and calcined for 2 hours at 500° C. Toluene adsorption capacity of the agglomerated pellets was 0.223 g/g, which was equivalent to 95.7 mass % of the content of zeolite X in agglomerated pellets.

The pellets obtained after in-situ crystallization treatment were ion-exchanged and dried for dehydration according to the step (4) of example 1 to obtain comparative adsorbent B-2 and its ignition loss was 5.1 mass % as measured after calcination at 600° C. for 2 hours. The composition of the adsorbent, the volume and the size distribution of pores as measured by mercury porosimetry, and other physical properties were recorded in table 1.

Example 7

Adsorptive separation of para-xylene using adsorbent A-2 was carried out in a small simulated moving bed with continuous countercurrent.

Figure 2:
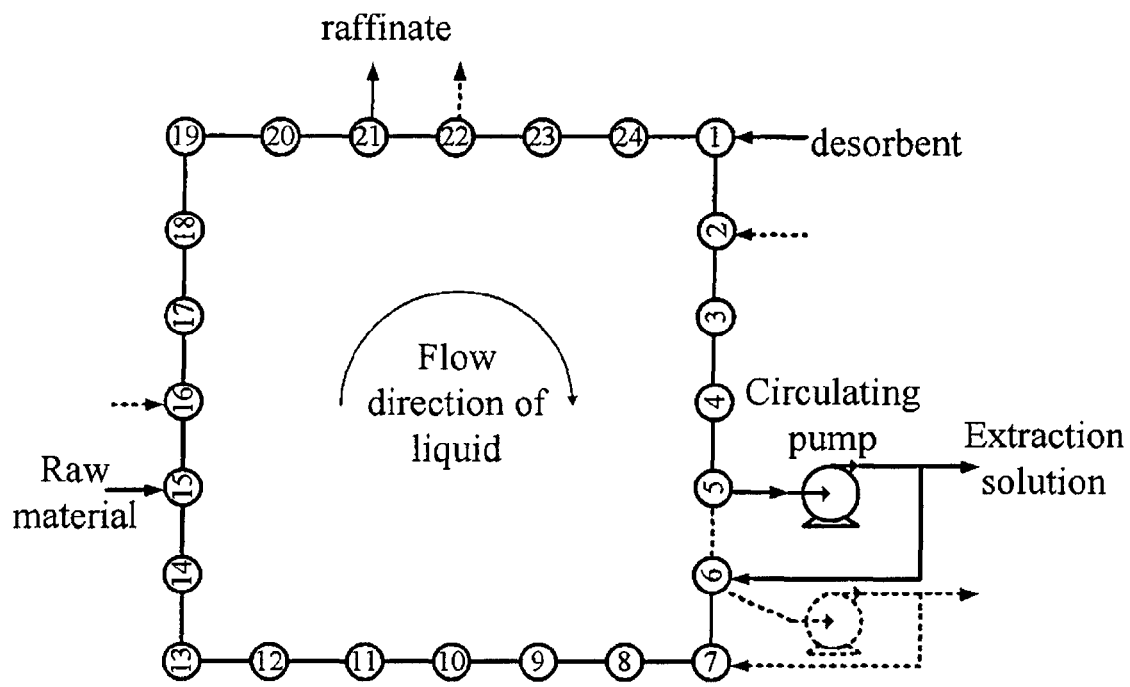
FIG. 2 is a schematic figure of adsorptive separation according to the present invention.

Said small simulated moving bed comprises 24 adsorptive columns in series, wherein each column is 195 mm long and has an internal diameter of 30 mm. The total amount of the loaded adsorbent was 3300 ml. As showed in FIG. 2, the first and the last of 24 columns in series were connected together by a circulating pump to form a closed circuit. In FIG. 2, 24 columns were separated into four zones by four strands of in-feeding or out-feeding, i.e., the adsorptive raw material, the desorbent, the extraction solution and the raffinate. That is, seven adsorptive columns between the adsorptive raw material (column 15) and the raffinate (column 21) constitutes adsorptive zone, nine adsorptive columns between the extraction solution (column 6) and the adsorptive raw material (column 14) constitutes purification zone, five adsorptive columns between the desorbent (column 1) and the extraction solution (column 5) constitutes desorption zone, and three adsorptive columns between the raffinate (column 22) and the desorbent (column 24) constitutes buffer zone. The temperature in the whole adsorptive system was controlled at 177° C., and the pressure was controlled at 0.8 MPa.

During operation, the desorbent para-diethylbenzene at a flow rate of 1420 mL/h and the absorptive raw material at a flow rate of 1190 mL/h were fed continuously into the above-mentioned simulated moving bed, respectively, and the extraction solution at a flow rate of 710 mL/h and the raffinate at a flow rate of 1900 mL/h were taken out of the device, respectively. Said absorptive raw material consists of 9.3 mass % ethylbenzene, 18.5 mass % para-xylene, 45.4 mass % meta-xylene, 17.4 mass % ortho-xylene and 9.4 mass % non-aromatic hydrocarbon component. According to the principle of simulated countercurrent chromatography, when the flow rate of circulating pump was set at 4580 mL/h, the positions of four strands of stuffs shift forward one adsorptive column in the same direction as the liquid flow direction per 70 seconds. Under stable operating conditions, the purity of para-xylene obtained was 99.75 mass % and the recovery was 99.0 mass %. The productivity of para-xylene was calculated as 0.066 $m^3$ of para-xylene absorptive-separated per $m^3$ of the adsorbent per hour.

Example 8

Adsorbent A-6 was fed into a small moving bed, and adsorptive separation of para-xylene was carried out according to the procedure described in Example 7. Under stable operating conditions, the purity of para-xylene obtained was 99.80 mass %, and the recovery was 98.4 mass %. The productivity of para-xylene was calculated as 0.0656 $m^3$ of para-xylene absorptive-separated by per $m^3$ of the adsorbent per hour.

Comparative Example 3

Comparative adsorbent B-2 was fed into a small moving bed, and adsorptive separation of para-xylene was carried out according to the procedure described in Example 7. Under stable operating conditions, the purity of para-xylene obtained was 99.71 mass %, and the recovery was 90.5 mass %. The productivity of para-xylene was calculated as 0.0604 $m^3$ of para-xylene absorptive-separated by per $m^3$ of the adsorbent per hour.

TABLE 1

| | Example | | | | | | Comparative example 1 | Comparative example 2 |
|---|---|---|---|---|---|---|---|---|
| | 1 | 2 | 3 | 4 | 5 | 6 | | |
| Adsorbent | A-1 | A-2 | A-3 | A-4 | A-5 | A-6 | B-1 | B-2 |
| Content of zeolite X, mass % | 95.7 | 97.9 | 96.2 | 95.3 | 97.0 | 97.0 | 93.2 | 94.9 |
| Content of $Na_2O$, mass % | 0.58 | 0.55 | 0.63 | 0.57 | 0.52 | 0.44 | 0.61 | 0.57 |
| Crash percent under pressure, mass % | 10.2 | 11.0 | 9.5 | 9.2 | 10.7 | 10.8 | 9.8 | 10.0 |
| Total pore volume measured by mercury porosimetry, mL/g | 0.276 | 0.315 | 0.270 | 0.268 | 0.293 | 0.297 | 0.195 | 0.227 |
| Volume of pores with pore | 0.180 | 0.228 | 0.178 | 0.181 | 0.219 | 0.222 | 0.107 | 0.131 |

TABLE 1-continued

| | Example | | | | | | Comparative example 1 | Comparative example 2 |
|---|---|---|---|---|---|---|---|---|
| | 1 | 2 | 3 | 4 | 5 | 6 | | |
| diameters from 100 to 500 nm, mL/g | | | | | | | | |
| Rate of Volume of pores with pore diameters from 100 to 500 nm to total pore volume, % | 65.2 | 72.4 | 65.9 | 67.5 | 74.7 | 74.7 | 56.9 | 57.7 |
| Volume of pores with pore diameters larger than 500 nm, mL/g | 0.034 | 0.043 | 0.028 | 0.025 | 0.038 | 0.041 | 0.036 | 0.048 |
| Volume Percentage of pores with pore diameters larger than 500 nm in total pores, % | 12.3 | 13.7 | 10.4 | 9.3 | 13.0 | 13.8 | 18.5 | 21.1 |
| Mass transfer rate for internal diffusion, min | 5.1 | 4.0 | 4.9 | 5.0 | 4.5 | 4.3 | 6.9 | 6.2 |

The invention claimed is:

1. An agglomerated zeolite adsorbent, comprising 95-99.5 mass % of X zeolite and 0.5-5.0 mass % of binder, wherein the exchangeable cationic sites of said X zeolite are occupied by Group IIA metal or Group IIA metal and K, the total pore volume of said adsorbent is no less than 0.26 mL/g as measured by mercury porosimetry, the volume of pores with pore diameters from 100 to 500 nm is at least 70% based on the total pore volume.

2. The adsorbent of claim 1, wherein said Group IIA metal is barium.

3. The adsorbent of claim 1, wherein the total pore volume of said adsorbent is no less than 0.28 mL/g as measured by mercury porosimetry, and the volume of pores with pore diameters from 100 to 500 nm is at least 70% based on the total pore volume.

4. The adsorbent of claim 1, wherein the volume of pores with pore diameters larger than 500 nm is from 5% to 15% based on the total pore volume.

5. The adsorbent of claim 1, wherein the molar ratio of barium oxide to potassium oxide in the adsorbent is from 20 to 60 when the cations of X zeolite in said adsorbent are Ba and K.

6. The adsorbent of claim 1, wherein the content of sodium oxide in the adsorbent is no more than 1.0 mass % after ion exchange, and the ignition loss of the adsorbent is no more than 7.0 mass % after calcination at 600° C.

7. The adsorbent of claim 1, wherein the mean particulate size of crystal grains of said X zeolite is from 0.1 micron to 1.0 micron.

8. The adsorbent of claim 1, wherein said binder is uncrystallized matrix of kaolin family minerals after in-situ crystallization.

9. A process for producing the adsorbent of claim 1, including the following steps:
(1) combing zeolite NaX or NaKX with zeolitizable clay and shaping auxiliary to provide a mixed powder, wherein the mass ratio of zeolite NaX or NaKX to zeolitizable clay is 88-95:12-5, adding water-soluble carbonate or water-soluble polymer compound as a pore-forming agent to the mixed powder to allow it to agglomerate into pellet by tumbling, followed by drying and calcining;
(2) treating the calcined pellet of step (1) with sodium hydroxide solution or mixed solution of sodium hydroxide and sodium silicate at 90-100° C. to allow the clay therein to crystallize into X zeolite in situ, followed by drying and calcinating;
(3) cation-exchanging the resultant of step (2) with solution of soluble salt of Group IIA metal or with mixed solution of potassium salt and soluble salt of Group IIA metal, followed by activation.

10. The process of claim 9, wherein said zeolitizable clay in the step (1) is kaolin family mineral.

11. The process of claim 10, wherein said kaolin family mineral is selected from kaolinite, dickite, nacrite, endellite or mixture thereof.

12. The process of claim 9, wherein said shaping auxiliary in the step (1) is one or more selected from lignin, sesbania powder, dry starch, carboxymethyl cellulose, and activated carbon.

13. The process of claim 9, wherein the ratio between the mass of shaping auxiliary added in step (1) and the total mass of said NaX or NaKX zeolite and the clay is from 1% to 8%.

14. The process of claim 9, wherein said water-soluble carbonate in the step (1) is ammonium carbonate, sodium carbonate or sodium bicarbonate.

15. The process of claim 9, wherein said water-soluble polymer compound in the step (1) is one or more selected from polyacrylamide, polyvinyl alcohol and polyethylene glycol.

16. The process of claim 9, wherein an aqueous solution formulated from said pore-forming agent is added to the mixed powder, and the concentration of aqueous pore-forming agent solution is from 0.5 mass % to 10.0 mass %, and the aqueous pore-forming agent solution added is from 10% to 40% of the total mass of the mixed powder.

17. The process of claim 9, wherein the concentration of the sodium hydroxide solution in the step (2) is from 1.0 mol/L to 4.0 mol/L, the content of sodium oxide in said mixed solution of sodium hydroxide and sodium silicate is from 3.0 mass % to 8.0 mass %, and the content of silicon dioxide in said mixed solution of sodium hydroxide and sodium silicate is from 1.0 mass % to 7.0 mass %.

18. The process of claim 9, wherein said soluble salt of Group IIA metal in the step (3) is barium nitrate or barium chloride, and the potassium salt is potassium chloride or potassium nitrate.

19. The process of claim 9, wherein said activation in the step (3) is carried out under nitrogen gas stream or air stream, and the activation temperature is from 180° C. to 250° C.

* * * * *